US012150936B2

(12) United States Patent
Roberts

(10) Patent No.: US 12,150,936 B2
(45) Date of Patent: Nov. 26, 2024

(54) COMPOSITIONS AND METHODS FOR TREATING ARRHYTHMOGENIC CARDIOMYOPATHY

(71) Applicant: Venca Research, Inc., Burlington (CA)

(72) Inventor: Jason Roberts, Hamilton (CA)

(73) Assignee: Venca Research, Inc., Burlington (CA)

( * ) Notice: Subject to any disclaimer, the term of this patent is extended or adjusted under 35 U.S.C. 154(b) by 0 days.

(21) Appl. No.: 17/670,150

(22) Filed: Feb. 11, 2022

(65) Prior Publication Data
US 2022/0249448 A1  Aug. 11, 2022

Related U.S. Application Data

(60) Provisional application No. 63/148,346, filed on Feb. 11, 2021.

(51) Int. Cl.
*A61K 31/433* (2006.01)
*A61P 9/04* (2006.01)

(52) U.S. Cl.
CPC .............. *A61K 31/433* (2013.01); *A61P 9/04* (2018.01)

(58) Field of Classification Search
CPC ................................ A61K 31/433; A61P 9/04
See application file for complete search history.

(56) References Cited

FOREIGN PATENT DOCUMENTS

WO    WO-0185685 A1    11/2001
WO    WO-2006045581 A1    5/2006

OTHER PUBLICATIONS

Asimaki, A., et al., "Identification of a New Modulator of the Intercalated Disc in a Zebrafish Model of Arrhythmogenic Cardiomyopathy," Science Translational Medicine, Jun. 11, 2014, 6(240):1-32.
Baturova, M.A., et al., "Atrial Fibrillation as a Clinical Characteristic of Arrhythmogenic Right Ventricular Cardiomyopathy: Experience from the Nordic ARVC Registry," International Journal of Cardiology, Jan. 2020, 298:39-43.
Camm, C.F., et al., "Premature Ventricular Contraction Variability in Arrhythmogenic Right Ventricular Dysplasia/Cardiomyopathy," Journal of Cardiovascular Electrophysiology, Jan. 2015, 26(1):53-57.
Chelko, S.P., et al., "Central Role for GSK3B in the Pathogenesis of Arrhythmogenic Cardiomyopathy," JCI insight, Apr. 21, 2016, 1(5):1-20.
Dominguez, J. M., et al., "Evidence for Irreversible Inhibition of Glycogen Synthase Kinase-3β by Tideglusib," The Journal of Biological Chemistry, Jan. 6, 2012, 287(2):893-904.
International Search Report and Written Opinion for International Application No. PCT/CA2022/050205, mailed Apr. 20, 2022, 12 pages.
Luna-Medina, R., et al., "NP031112, A Thiadiazolidinone Compound, Prevents Inflammation and Neurodegeneration under Excitotoxic Conditions: Potential Therapeutic Role in Brain Disorders," The Journal of Neuroscience, May 23, 2007, 27(21):5766-5776.
Malik, N., et al., "Right Ventricular Strain Predicts Structural Disease Progression in Patients With Arrhythmogenic Right Ventricular Cardiomyopathy," Journal of the American Heart Association, Apr. 2020, 9(7):e015016:1-9.
Martinez, A., et al., "First Non-ATP Competitive Glycogen Synthase Kinase 3 β (GSK-3β) Inhibitors: Thiadiazolidinones (TDZD) as Potential Drugs for the Treatment of Alzheimer's Disease," Journal of Medicinal Chemistry, Mar. 14, 2002, 45(6):1292-1299.
Roberts, J.D., et al., "Ankyrin-B Dysfunction Predisposes to Arrhythmogenic Cardiomyopathy and is Amenable to Therapy," The Journal of Clinical Investigation, Jul. 2, 2019, 129(8):3171-3184.
Tideglusib, CAS Registration No. 865854-05-3, "2-(1-naphthalenyl)-4-(phenylmethyl)-1,2,4-thiadiazolidine-3,5-dione," Product Information, Cayman Chemical, 2014, 1 page.
Chen, C. et al. "Aberrant activation of Wnt/β-catenin signaling drives proliferation of bone sarcoma cells," Oncotarget, May 11, 2015, 6(19):17570-17583.
Dominguez, F. et al. "Early Preventive Treatment With Enalapril Improves Cardiac Function and Delays Mortality in Mice With Arrhythmogenic Right Ventricular Cardiomyopathy Type 5," Circ. Heart Fail., Sep. 2021, 998-1008.
Horrigan, J. et al. "A Phase 2 Study of AMO-02 (Tideglusib) in Congenital and Childhood-Onset Myotonic Dystrophy Type 1 (DM1)," Pediatric Neurology, 2020, 112:84-93.
Lovestone, S. et al. "A Phase II Trial of Tideglusib in Alzheimer's Disease," Journal of Alzheimer's Disease, 2015, 45:75-88.
Tolosa E, et al. "A phase 2 Trial of the GSK-3 Inhibitor Tideglusib in Progressive Supranuclear Palsy", Movement Disorders, 2014, 29(4):470-478.

*Primary Examiner* — Kamal A Saeed
(74) *Attorney, Agent, or Firm* — COOLEY LLP; Cynthia A. Kozakiewicz; Taylor D. Canady

(57) ABSTRACT

The present invention provides methods of treating arrhythmogenic cardiomyopathy (ACM) by administration of a thiadiazolidindione or a derivative thereof such as for example tideglusib or NPE 100928.

29 Claims, No Drawings

COMPOSITIONS AND METHODS FOR TREATING ARRHYTHMOGENIC CARDIOMYOPATHY

RELATED APPLICATIONS

This application claims benefit of, and priority to, U.S. Ser. No. 63/148,346 filed on Feb. 11, 2021; the contents of which are hereby incorporated by reference in its entirety.

FIELD OF THE INVENTION

The present invention relates generally to the treatment and or prevention of arrhythmogenic cardiomyopathy (ACM), such as arrhythmogenic right ventricular cardiomyopathy (ARVC), by administration of a thiadiazolidindione.

BACKGROUND OF THE INVENTION

Arrhythmogenic cardiomyopathy (ACM) is a heritable form of structural heart disease characterized by myocardial fibrofatty infiltration. The majority of cases preferentially involve the right ventricle (RV), termed arrhythmogenic right ventricular cardiomyopathy (ARVC). Clinical variants characterized by early and greater LV involvement, which may parallel (i.e., biventricular ACM) or exceed (i.e., left-dominant ACM) the severity of RV involvement, have been reported.

Affected patients are vulnerable to malignant ventricular arrhythmias, sudden cardiac death (SCD), and heart failure. Development of an ACM phenotype may be influenced by both genetic and environmental factors, such as exercise. Although an increasingly diverse set of genes have been implicated in ACM, its most prominent genetic culprits are constituents of the desmosome, a specialized cellular structure within the intercalated disc that mediates intercellular adhesion.

Despite progress in understanding the genetic underpinnings of ACM, insight into its pathophysiology remains limited. This lack of understanding of its operative biological pathways has precluded development of tailored treatments, leading to approaches to medical therapy being largely adopted from those utilized for more common forms of cardiomyopathy. Such treatments include an implantable cardioverter defibrillator (ICD), antiarrhythmic agents, β-blockers, and heart failure drug therapy. However, these treatment measures are palliative, not curative, and are often inadequate.

Therefore, a need exists for development of therapies that target the underlying pathophysiology of patients with ACM. This invention fills that unmet need.

SUMMARY OF THE INVENTION

In various aspects the present disclosure provides a method of treating or alleviating a symptom of arrhythmogenic cardiomyopathy (ACM) in a subject by administering a thiadiazolidindione or a derivative thereof. The thiadiazolidindione or a derivative thereof include inhibitors of glycogen synthase kinase 3β (GSK3β). The GSK3β inhibitor is preferably a selective inhibitor. The GSK3β inhibitor is preferably a reversible inhibitor. Alternatively, the GSK3β inhibitor is an irreversible inhibitor.

Exemplary thiadiazolidindiones for use in the methods of the present invention include tideglusib or NPE100928.

The subject has or is at risk of developing ACM. Symptoms of ACM include ventricular tachycardia, implantable cardioverter-defibrillator (ICD) shock, lung congestion, fluid retention, fatigue, heart murmurs, rapid heartbeat, arrhythmias, chest pain, light-headedness, fainting, dyspnea, peripheral edema, abdominal distention, myocardial fibrofatty infiltration, embolization, heart failure or sudden cardiac death (SCD). In some aspects, the ACM is arrhythmogenic right ventricular cardiomyopathy (ARVC).

In other aspects, the disclosure provides methods of reducing the number of premature ventricular contractions (PVCs) in a subject by administering a thiadiazolidindione or a derivative thereof.

In yet another aspect, the disclosure provides methods of improving ventricular function by administering a thiadiazolidindione or a derivative thereof.

The subject has arrhythmogenic cardiomyopathy (ACM) such as for example, arrhythmogenic right ventricle cardiomyopathy (ARVC). The subject has an implantable cardioverter defibrillator (ICD).

The administration of a thiadiazolidindione or a derivative thereof reduces the number of electrical shocks delivered by the ICD to the subject.

In various aspects the administration of a thiadiazolidindione or a derivative thereof improves a measure of ventricular function in the subject, such as for example ventricular strain, systolic function or diastolic function.

Ventricular function is measured by echocardiography (echo), ambulatory rhythm (Holter) monitoring, cardiac CT scan, or cardiac magnetic resonance imaging.

The subject has one of more mutations in a gene associated with ACM. Genes associated with ACM is for example a gene encoding a component of the desmosome. Genes encoding a component of the desmosome include for example, Plakophilin-2 (PKP2), Desmoplakin (DSP), Desmoglein-2 (DSG2), Desmocollin-2 (DSC2), or Plakoglobin (JUP). Other gene associated with ACM include, but are not limited to, Transmembrane protein 43 (TMEM43), Catenin Alpha 3 (CTNNA3), Desmin (DES), Lamin A/C (LMNA), Phospholamban (PLN), Ryanodine Receptor 2 (RYR2), Transforming growth factor beta-3 (TGFB3), Titin (TTN), Filamin C (FLNC), RNA Binding Motif Protein 20 (RBM20), Sodium Voltage-Gated Channel Alpha Subunit 5 (SCN5A), or BAG Cochaperone 3 (BAG3).

In a further aspect, the method of treating or alleviating a symptom of atrial fibrillation in a subject comprising administering a thiadiazolidindione or a derivative thereof to a subject having or at risk of developing atrial fibrillation. The subject has ACM. Symptoms of atrial fibrillation include for example, rapid heartbeat, arrythmias, chest pain, light-headedness, fainting, dyspnea, heart failure, stroke or death.

The disclosure further provides methods of reducing the number of premature atrial contractions or improving atrial function by administering a thiadiazolidindione or a derivative thereof. The subject has ACM or atrial fibrillation (AF).

In the various methods of the disclosure, the subject is a human, a canine, a feline, or an equine. Preferably, the subject us human.

The thiadiazolidindione or a derivative thereof is administered orally. For example, a thiadiazolidindione or a derivative thereof is administered at a daily dose of between about 100 mg to about 1500 mg. An Exemplary, daily dose is about 1000 mg or about 600 mg. The daily dose is administered in a single dose, two doses, three doses or four doses.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

DETAILED DESCRIPTION OF THE INVENTION

The invention is based in part upon the discovery that the thiadiazolidindione, tideglusib prevents electrical, molecular and structural changes associated with arrhythmogenic cardiomyopathy (ACM). The ability of tideglusib to halt, and even reverse, ACM disease progression highlights the potential for targeted therapy to treat this life-threatening condition.

Accordingly, the present disclosure provides methods for treating, preventing, or alleviating a symptom of ACM by administering a thiadiazolidindione to a patient.

ACM is a predominantly genetic-based heart disease characterized by right, but also recently left, ventricular dysfunction, and fibro-fatty replacement of the myocardium resulting in fatal/severe ventricular arrhythmias leading to sudden cardiac death in young people and athletes. ACM is thought to be a rare disease as it occurs in 1 in 2500-5000 people, although the prevalence may be higher as some patients are undiagnosed or misdiagnosed due to diagnostic challenges.

At present there are no treatments for ACM that address its underlying pathophysiology. As a result, treatment strategies for ACM patients are primarily directed at preventing sudden cardiac death secondary to malignant ventricular arrhythmias, which most often involves insertion of an implantable cardioverter defibrillator (ICD) following an arrhythmic event or when accepted risk factors develop. Treatment of malignant ventricular arrhythmias with ICD shocks is painful, which necessitates therapy with anti-arrhythmic drugs and/or catheter ablation. Anti-arrhythmic drugs (e.g., flecainide, sotalol, amiodarone, and beta-blockers) often have limited efficacy and also carry the potential for unwanted side effects. When anti-arrhythmic drugs become ineffective and patients begin experiencing breakthrough arrhythmic events requiring ICD shocks, more invasive treatment through cardiac catheter ablation is often required. This invasive procedure, which often requires both endocardial and epicardial approaches, carries significant risk and may have modest efficacy. Despite these therapeutic options, affected patients remain at risk of heart failure and death and a significant proportion ultimately require heart transplantation for refractory ventricular arrhythmias.

Thiazolidinediones also known as glitazones after the prototypical drug ciglitazone, are a class of heterocyclic compounds consisting of a five-membered C3NS ring. Thiazolidinediones or TZDs act by activating PPARs (peroxisome proliferator-activated receptors), a group of nuclear receptors, specific for PPARγ (PPAR-gamma, PPARG). They are thus the PPARG agonists subset of PPAR agonists.

The invention includes administering to a subject a composition comprising a thiadiazolidindione.

In some embodiments, the methods described herein comprise administering to a subject in need thereof an effective amount of a compound of Formula (I):

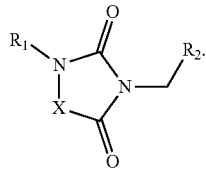

Formula I or a pharmaceutically acceptable salt, hydrate, solvate or stereoisomer thereof, wherein:

$R^1$ and $R^2$ are each independently selected from H, $C_{1-7}$ alkyl, $C_{3-7}$ cycloalkyl, $C_{3-10}$ heterocyclyl, aryl, or heteroaryl, wherein each group is optionally substituted by halo, alkyl, alkoxy, cycloalkyl, aryl, or heteroaryl; and X is selected from oxygen, nitrogen, or sulfur.

As used herein, the term "halo" means halogen and includes fluoro, chloro, bromo and iodo.

As used herein, the term "alkoxy" means an alkyl radical attached through an oxygen linking atom, represented by —O-alkyl. Examples include a methoxy, ethoxy, propoxy, and butoxy.

As used herein, the term "alkyl" means saturated or unsaturated aliphatic straight-chain or branched monovalent hydrocarbon radical. Unless otherwise specified, an alkyl group typically has 1-7 carbon atoms, i.e. $C_{1-7}$ alkyl.

As used herein, the term "cycloalkyl" means a cyclic saturated or unsaturated hydrocarbon ring system. It can be monocyclic, bicyclic or tricyclic (e.g., a fused or bridged bicyclic or tricyclic ring). Unless otherwise specified, an cycloalkyl group typically has 3-7 carbon atoms, i.e. $C_{3-7}$ cycloalkyl.

As used herein, the term "heterocyclyl" means a saturated or unsaturated non-aromatic 3-10 membered ring radical containing from 1 to 4 ring heteroatoms, which may be the same or different, selected from N, O, or S. It can be monocyclic, bicyclic or tricyclic (e.g., a fused or bridged bicyclic or tricyclic ring). A heterocyclic ring optionally contains one or more double or triple bonds and/or is optionally fused with one or more aromatic rings.

As used herein, the term "aryl", means aromatic ring groups having five to ten ring carbon atoms. It can be monocyclic, bicyclic or tricyclic (e.g., a fused or bridged bicyclic or tricyclic ring).

As used herein, the term "heteroaryl", means aromatic ring groups having five to ten ring atoms selected from carbon and at least one (typically 1 to 4, more typically 1 or 2) heteroatoms (e.g., oxygen, nitrogen or sulfur). "Heteroaryl" includes monocyclic rings and polycyclic rings in which a monocyclic heteroaromatic ring is fused to one or more other aromatic or heteroaromatic rings. "Heteroaryl" includes monocyclic and bicyclic ring systems.

If a group is described as being "substituted," a non-hydrogen substituent replaces a hydrogen on a carbon or nitrogen of the substituent. Thus, for example, a substituted alkyl is an alkyl wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent can be identical or different (unless otherwise stated). As used herein, many moieties (e.g., alkyl, cycloalkyl, or a heterocyclic ring) are referred to as being "optionally substituted". When a moiety is modified by this term, unless otherwise noted, it denotes that any portion of the moiety that is known to one skilled in the art as being available for substitution can be substituted, which includes one or more substituents. If more than one substituent is present, then each substituent is independently selected. Such means for substitution are well-known in the art and/or taught by the instant disclosure. The optional substituents can be any substituents that are suitable to attach to the moiety. A person of ordinary skill in the art will recognize that the compounds and definitions provided do not include impermissible substituent patterns (e.g., methyl substituted with 5 different groups, and the like). Such impermissible substitution patterns are clearly recognized by a person of ordinary skill in the art.

It is to be understood that, for the compounds of the present disclosure being capable of further forming salts, all of these forms are also contemplated within the scope of the claimed disclosure.

As used herein, the term "pharmaceutically acceptable salts" refer to derivatives of the compounds of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids.

It is to be understood that the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, the term "solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water, the solvate formed is a hydrate; and if the solvent is alcohol, the solvate formed is an alcoholate. Hydrates are formed by the combination of one or more molecules of water with one molecule of the substance in which the water retains its molecular state as $H_2O$.

Thiadiazolidindiones useful in the methods of the invention include for example, include inhibitors of glycogen synthase kinase 3β (GSK3β). The GSK3β inhibitor is preferably a selective inhibitor. The GSK3β inhibitor is preferably a reversible inhibitor. Alternatively, the GSK3β inhibitor is an irreversible inhibitor.

Exemplary thiadiazolidindiones include the compound of Formula II, Formula III or derivatives thereof. As used herein, the term "derivative" refers to compounds that have a common core structure and are substituted with various groups as described herein.

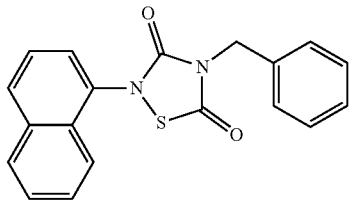

Formula II

The structure represented by Formula II is Tideglusib. Tideglusib (CAS No. 865854-05-3) or 4-benzyl-2-(naphthalen-1-yl)-1,2,4-thiadiazolidine-3,5-dione is also known as NP-031112, NP-12 compound, Nypta®, or Zentylor™.

Tideglusib is a member of the class of thiadiazolidines that is 1,2,4-thiadiazolidine-3,5-dione which is substituted by a naphthalen-1-yl group at position 2 and by a benzyl group at position 4. Tideglusib is a selective and irreversible non-ATP competitive inhibitor of glycogen synthase kinase 3β (GSK3β) and has a role as an EC 2.7.11.26 (tau-protein kinase) inhibitor, a neuroprotective agent, an anti-inflammatory agent and an apoptosis inducer. Tideglusib has been under clinical investigation for the treatment of Alzheimer's disease and progressive supranuclear palsy. Tideglusib is currently under investigation for myotonic dystrophy.

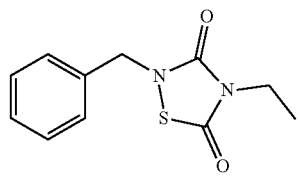

Formula III

The structure represented by Formula III is NPE100928 NPE100928 is a member of the class of thiadiazolidines that is 1,2,4-thiadiazolidine-3,5-dione which is substituted by a benzyl group at position 2 and by a ethyl group at position 4. NPE100928 is an irreversible non-ATP competitive inhibitor of glycogen synthase kinase 3β (GSK3β)

NPE 100928 (CAS No. 865854-05-3) or 2-Benzyl-4-ethyl-1,2,4 thiadiazolidine-3,5-dione is also known as AMO-05.

The invention includes administering to a subject a composition comprising a thiadiazolidindione. A thiadiazolidindione such as tideglusib or NPE100928 thereof can be provided to a subject in need thereof alone or as such as an active ingredient, in a pharmaceutical formulation. The subject in need thereof has, is predisposed, or at risk of developing cardiomyopathy. Subjects having cardiomyopathy can be identified by a physician using current methods of diagnosing cardiomyopathy. Tests that may aid in a diagnosis of, e.g. cardiomyopathy include, but are not limited to, echocardiography (echo), electrocardiogram (ECG), ambulatory rhythm (Holter) monitoring, cardiac CT scan, and cardiac magnetic resonance imaging. A family history of cardiomyopathy, or exposure to risk factors for cardiomyopathy can also aid in determining if a subject is likely to have cardiomyopathy or in making a diagnosis of cardiomyopathy.

Mutations in a gene encoding a component of the desmosome can also aid in determining if a subject is likely to have cardiomyopathy or in making a diagnosis of cardiomyopathy. Genes encoding a component of the desmosome include, for example, Plakophilin-2 (PKP2), Desmoplakin (DSP), Desmoglein-2 (DSG2). Desmocollin-2 (DSC2), and Plakoglobin (JUP). Other genes that have been implicated in ACM include, for example, Transmembrane protein 43 (TMEM43). Catenin Alpha 3 (CTNNA3). Desmin (DES), Lamin A/C (LMNA). Phospholamban (PLN). Ryanodine Receptor 2 (RYR2), Transforming growth factor beta-3 (TGFB3), Titin (TTN). Filamin C (FLNC). RNA Binding Motif Protein 20 (RBM20), Sodium Voltage-Gated Channel Alpha Subunit 5 (SCN5A), or BAG Cochaperone 3 (BAG3).

In some aspects, the subject has had an implantable cardioverter defibrillator (ICD) inserted due to a perceived risk of life-threatening arrhythmias or has previously suffered a cardiac arrest, sustained ventricular tachycardia, or episodes of worrisome syncope or pre-syncope. In other aspects, the patient has begun to manifest clinical features of the disease, including frequent premature ventricular contractions (PVCs) or non-sustained ventricular tachycardia on ambulatory monitoring, electrocardiogram (ECG) abnormalities, such as an epsilon wave or precordial T-wave inversion, or evidence of cardiac dysfunction on imaging modalities, such as echocardiography and cardiac magnetic resonance imaging. In other aspects, the patient has a damaging genetic variant that places them at risk of developing ACM and suffering from life-threatening arrhythmias Non-sustained ventricular tachycardia is defined as more than 3 beats of ventricular origin at a rate greater than 100 beats per minute that lasts less than 30 seconds in duration. When the rhythm lasts longer than 30 seconds or hemodynamic instability occurs in less than 30 seconds, it is considered sustained ventricular tachycardia.

The subject in need thereof has ≥200 PVCs per 24 hours. For example the subjects has a PVCs burden of about ≥200 PVCs; ≥250 PVCs; ≥300 PVCs; ≥350 PVCs; ≥400 PVCs; ≥450 PVCs; ≥500 PVCs≥600 PVCs, ≥700 PVCs, ≥800 PVCs, ≥900 PVCs, ≥1000) PVCs or more in a 24 hour period.

As used herein, "cardiomyopathy" refers to a disease of the myocardium associated with ventricular dysfunction as defined by the World Health Organization.

The methods described herein are used to treat, prevent of alleviate a symptom of arrhythmogenic cardiomyopathy, a subtype of cardiomyopathy associated with a prominent risk of arrhythmia.

As used herein, "alleviating a symptom of a cardiomyopathy" is ameliorating any condition or symptom associated with the cardiomyopathy. As compared with an equivalent untreated control, such reduction is by at least 1%, 2%, 3%, 4%, 5%, 10%, 20%, 40%, 50%, 60%, 80%, 90%, 95%, 99% or more as measured by any standard technique.

Symptoms and/or complications of cardiomyopathy which characterize these conditions and aid in diagnosis are well known in the art and include but are not limited to, lung congestion, fluid retention, fatigue, heart murmurs, rapid heartbeat, arrhythmias, chest pain, light-headedness, fainting, dyspnea, peripheral edema, abdominal distention, embolization, myocardial fibrofatty infiltration, heart failure or sudden cardiac death (SCD).

In various aspects the methods of the invention reducing the number of premature ventricular contractions (PVCs) and/or improve ventricular function.

PVCs are measured by an electrocardiographic device such as for example a Holter monitor. A reduction of PVCs means a reduction of ≥1%, ≥2%, ≥4%, ≥5%, ≥10%, ≥15%, ≥20%, ≥25%, ≥30%, ≥35%, ≥40%≥45%, ≥50%, or more compared to the number of PVC prior to treatment (i.e the subjects baseline PVC rate). The number of PVCs and the reduction thereof can be measured in a period of 24 hrs, 48 hrs, 72 hrs., 96 hrs, 120 hrs, or more. Alternatively, the number of PVCs and the reduction thereof can be measured in a period of 1 day, 2 days, 3 days, 4 days, 5 days, 6 days, 7 days or more. The number of PVCs and the reduction thereof can be measured in a period of 1 week, 2 weeks, 3 weeks, 4 weeks, or more. The number of PVCs and the reduction thereof can be measured in a period of 1 month, 2 months, 3 months, 4 months, 5 months, 6 months, or more.

Improvement in ventricular function as used herein means an improvement in ejection fraction of ≥1, ≥2, ≥4, ≥5, 10≥10%, ≥15%, ≥20%, ≥25%, ≥30%, ≥35%, ≥40%≥45%, ≥50%, or more. In some aspects, a reduction in ventricular (e.g. right ventricular or left ventricular) end diastolic diameter.

Tideglusib or NPE100928 treatment also results in the reduction of: implantable cardioverter-defibrillator (ICD) therapies, sustained ventricular tachycardia (VT); the need for additional anti-arrhythmic drugs (beyond a beta-blocker); the need for a VT ablation procedure; the need for a heart transplantation, emergency room visits and hospitalizations; incident atrial fibrillation; non-sustained ventricular tachycardia (NSVT); atrial ectopy, sudden cardiac death, heart-related mortality, and all-cause mortality.

A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, injection or topical administration.

As used herein, "arrhythmia" refers to any of a group of conditions in which there is abnormal electrical activity in the heart. This can cause the heart beat to be too fast (tachycardia). Arrhythmia can affect the atria and/or the ventricles and occur at any age.

As used herein. "arrhythmogenic right ventricular cardiomyopathy (ARVC)" refers to heart disease characterized by myocardial fibrofatty infiltration. ARVC is a nonischemic cardiomyopathy that primarily involves the right ventricle and arrhythmia.

In some embodiments, the methods described herein relate to treating a subject having or diagnosed as having cardiomyopathy with compound of Formula (I). Preferably a compound of Formula (II) or Formula (III) or a derivative thereof having GSK3β inhibitory activity. The GSK3β inhibitor a selective inhibitor. The GSK3β inhibitor is a reversible inhibiter or an irreversible inhibitor.

Administration can be local or systemic. As such, also described herein are pharmaceutical formulations containing an amount (such as an effective, least effective, and/or therapeutically effective amount) of tideglusib. NPE 100928 or a derivative thereof. In some embodiments, the pharmaceutical formulations contain a therapeutically effective amount of tideglusib, NPE 100928 or a derivative thereof. The pharmaceutical formulations described herein can be administered to a subject in need thereof.

An effective amount of a therapeutic compound is preferably from about 0.1 mg/kg to about 150 mg/kg. More preferably, 0.5 mg/kg to 10 mg/kg, even more preferably 1 mg/kg to 5 mg/kg. Effective doses vary, as recognized by those skilled in the art, depending on route of administration, excipient usage, and coadministration with other therapeutic treatments including use of other therapeutic agents for treating, preventing ACM.

For example, tideglusib, NPE 100928 or a derivative thereof is administered at a daily dose of 100 mg, 200 mg, 300 mg, 400 mg, 500 mg, 600 mg, 700 mg, 800 mg, 900 mg, 1000 mg, 1100 mg, 1200 mg, 1300, mg, 1400 mg, 1500 mg or more.

Doses may be administered once, or more than once daily. In some embodiments, it is preferred that the therapeutic compound is administered once a day, twice a day, three times a day, or four times a day. In some cases, chronic administration may be desired. The terms "chronic administration" or "administered chronically" mean prolonged drug administration for a duration of greater than three months.

The pharmaceutical compound is administered to such an individual using methods known in the art. Preferably, the compound is administered orally, rectally, nasally, topically or parenterally, e.g., subcutaneously, intraperitoneally, intramuscularly, and intravenously, preferably intravenously. The inhibitors are optionally formulated as a component of a cocktail of therapeutic drugs. Examples of formulations suitable for parenteral administration include aqueous solutions of the active agent in an isotonic saline solution, a 5% glucose solution, or another standard pharmaceutically acceptable excipient. Standard solubilizing agents such as PVP or cyclodextrins are also utilized as pharmaceutical excipients for delivery of the therapeutic compounds.

The therapeutic compounds described herein are formulated into compositions for other routes of administration utilizing conventional methods. For example, the therapeutic compounds are formulated in a capsule, a tablet, or a suspension added to water and stirred for oral administration. Capsules may contain any standard pharmaceutically acceptable materials such as gelatin or cellulose. Tablets may be formulated in accordance with conventional procedures by compressing mixtures of a therapeutic compound with a solid carrier and a lubricant. Examples of solid carriers include starch and sugar bentonite. The compound is administered in the form of a hard shell tablet or a capsule containing a binder, e.g., lactose or mannitol, conventional filler, and a tableting agent. Other formulations include an ointment, suppository, paste, spray, patch, cream, gel, resorbable sponge, or foam. Such formulations are produced using methods well known in the art.

Therapeutic compounds are effective upon direct contact of the compound with the affected tissue. Accordingly, the compound is administered topically. Alternatively, the therapeutic compounds are administered systemically.

EXAMPLES

Example 1: Evaluation of Tideglusib as a Targeted Therapy for Arrhythmogenic Right Ventricular Cardiomyopathy The primary objective of these studies will be to show that tideglusib reduces PVCs on Holter monitoring, improves ventricular function, reduces life-threatening ventricular arrhythmias such as ventricular tachycardia and ventricular fibrillation, reduces ICD therapies, including shocks, reduces atrial fibrillation, reduces the need for heart transplantation, reduces cardiovascular death, and reduces all cause mortality relative to placebo in patients with ACM at risk of arrhythmias and sudden cardiac death.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A method of treating or alleviating a symptom of arrhythmogenic cardiomyopathy (ACM) in a human, comprising administering tideglusib or NPE 100928.

2. A method of reducing the number of premature ventricular contractions (PVCs) in a human in need thereof comprising administering tideglusib or NPE 100928.

3. A method of improving ventricular function in a human in need thereof comprising administering tideglusib or NPE 100928.

4. A method of treating or alleviating a symptom of atrial fibrillation in a human comprising administering tideglusib or NPE 100928 to a human having or at risk of developing atrial fibrillation.

5. A method of reducing the number of premature atrial contractions in a human in need thereof comprising administering tideglusib or NPE 100928.

6. A method of improving atrial function in a human in need thereof comprising administering tideglusib or NPE 100928.

7. The method of claim 1, wherein the symptom of ACM is ventricular tachycardia, implantable cardioverter-defibrillator (ICD) shock, lung congestion, fluid retention, fatigue, heart murmurs, rapid heartbeat, arrhythmias, chest pain, light-headedness, fainting, dyspnea, peripheral edema, abdominal distention, myocardial fibrofatty infiltration, embolization, heart failure or sudden cardiac death (SCD).

8. The method of claim 2, wherein the human has arrhythmogenic cardiomyopathy (ACM).

9. The method of claim 1, wherein the ACM is arrhythmogenic right ventricular cardiomyopathy (ARVC).

10. The method of claim 8, wherein the ACM is arrhythmogenic right ventricular cardiomyopathy (ARVC).

11. The method of claim 1, wherein the human has an implantable cardioverter defibrillator (ICD).

12. The method of claim 1, wherein the administration of tideglusib or NPE 100928 reduces the number of electrical shocks delivered by the ICD to the human.

13. The method of claim 1, wherein the administration of tideglusib or NPE 100928 improves a measure of ventricular function in the human.

14. The method of claim 13, wherein the measure of ventricular function is ventricular strain, systolic function or diastolic function.

15. The method of claim 13, wherein the ventricular function is measured by echocardiography (echo), ambulatory rhythm (Holter) monitoring, cardiac CT scan, or cardiac magnetic resonance imaging.

16. The method of claim 1, wherein the human has one or more mutations in a gene associated with ACM.

17. The method of claim 16, wherein the gene associated with ACM is a gene encoding a component of the desmosome.

18. The method of claim 17, wherein the gene encodes, Plakophilin-2 (PKP2), Desmoplakin (DSP), Desmoglein-2 (DSG2), Desmocollin-2 (DSC2), or Plakoglobin (JUP).

19. The method of claim 17, wherein the gene associated with ACM is Transmembrane protein 43 (TMEM43), Catenin Alpha 3 (CTNNA3), Desmin (DES), Lamin A/C (LMNA), Phospholamban (PLN), Ryanodine Receptor 2 (RYR2), Transforming growth factor beta-3 (TGFB3), Titin (TTN), Filamin C (FLNC), RNA Binding Motif Protein 20 (RBM20), Sodium Voltage-Gated Channel Alpha Subunit 5 (SCN5A), or BAG Cochaperone 3 (BAG3).

20. The method of claim 4, wherein the symptom of atrial fibrillation is rapid heartbeat, arrythmias, chest pain, lightheadedness, fainting, dyspnea, heart failure, stroke or death.

21. The method of claim 5, wherein the human has atrial fibrillation (AF).

22. The method of claim 1, wherein the tideglusib or NPE 100928 is administered orally.

23. The method of claim 1, wherein the tideglusib or NPE 100928 is administered at a daily dose of between 100 mg to 1500 mg.

24. The method of claim 23, where the daily dose is about 1000 mg.

25. The method of claim 23, wherein the daily dose is about 600 mg.

26. The method of claim 23, wherein the daily dose is administered in a single dose.

27. The method of claim 23, wherein the daily dose is administered in two doses.

28. The method of claim 23, wherein the daily dose is administered in three doses.

29. The method of claim 23, wherein the daily dose is administered in four doses.

* * * * *